(12) United States Patent
Bender et al.

(10) Patent No.: US 6,498,183 B1
(45) Date of Patent: Dec. 24, 2002

(54) SUBSTITUTED INDOLE SULFONAMIDES AS ANITVIRAL AGENTS

(75) Inventors: Wolfgang Bender, Wuppertal (DE); Peter Eckenberg, Wuppertal (DE); Siegfried Goldmann, Wuppertal (DE); Michael Härter, Leverkusen (DE); Sabine Hallenberger, Boston, MA (US); Jürgen Reefschläger, Wuppertal (DE); Jörg Trappe, Monza (IT); Olaf Weber, Woodbridge, CT (US)

(73) Assignee: Bayer Aktiengesellschaft, Leverkusan (DE)

( * ) Notice: Subject to any disclaimer, the term of this patent is extended or adjusted under 35 U.S.C. 154(b) by 0 days.

(21) Appl. No.: 09/980,763

(22) PCT Filed: Apr. 18, 2000

(86) PCT No.: PCT/EP00/03492
§ 371 (c)(1),
(2), (4) Date: Feb. 27, 2002

(87) PCT Pub. No.: WO00/66553
PCT Pub. Date: Nov. 9, 2000

(30) Foreign Application Priority Data

Apr. 30, 1999 (DE) ........................................ 199 19 793

(51) Int. Cl.[7] ...................... A61K 31/44; C07D 209/08; A61P 31/22
(52) U.S. Cl. ........................ 514/415; 548/491; 548/503
(58) Field of Search ................................ 548/415, 503; 514/415

(56) References Cited

U.S. PATENT DOCUMENTS

| 3,482,971 A | 12/1969 | Bloom et al. |
| 3,622,603 A | 11/1971 | Bloom et al. ............. 260/397.7 |
| 3,925,347 A | 12/1975 | Huyffer ....................... 260/147 |
| 4,035,401 A | 7/1977 | Huyffer ................... 260/404.5 |
| 4,533,625 A | 8/1985 | Ichijima et al. .............. 450/552 |
| 4,595,780 A | 6/1986 | Ogata et al. .................. 564/79 |
| 5,026,690 A | 6/1991 | Kresken et al. ............. 514/155 |
| 6,180,796 B1 | 1/2001 | Morohashi et al. ......... 548/240 |

FOREIGN PATENT DOCUMENTS

| DE | 2902074 | 7/1979 |
| EP | 0284130 | 6/1991 |
| EP | 0614887 | 9/1994 |
| EP | 0684515 | 11/1995 |
| JP | 59174836 | 10/1984 |
| JP | 6122669 | 5/1994 |
| WO | 9009787 | 7/1990 |
| WO | 9420101 | 9/1994 |
| WO | 9807719 | 2/1998 |
| WO | 9854131 | 3/1998 |
| WO | 9937291 | 7/1999 |
| WO | 9937609 | 7/1999 |

OTHER PUBLICATIONS

Pant, U., Joshi, B., "Studies on 2–Hydroxy–3–Naphthoic Acid–1–Sulphonamides and 4–Hydroxy–3–Naphthoic Acid–1–Sulphonamides", J. Inst. Chemists, 48: 280–285 (1976).

Primary Examiner—Joseph K. McKane
Assistant Examiner—Andrea D. Small
(74) Attorney, Agent, or Firm—Jerrie L. Chiu

(57) ABSTRACT

The present invention relates to novel compounds which are suitable as pharmaceuticals, to processes for their preparation and to their use as pharmaceuticals, in particular as antiviral agents.

9 Claims, No Drawings

SUBSTITUTED INDOLE SULFONAMIDES AS ANITVIRAL AGENTS

This application is a 371 of PCT/EP00/03492 filed Apr. 18, 2000.

The present invention relates to novel compounds which are suitable as pharmaceuticals, to processes for their preparation and to their use as pharmaceuticals, in particular as antiviral agents.

α,β-Naphthyl-linked phenylsulphonamides are mainly disclosed in photographic publications [compare in this connection JP-06 122 669-A2, EP-684 515-A1; JP-59 174 836-A2, DE-2 902 074, U.S. Pat. No. 3,925,347, U.S. Pat. No. 4,035,401, U.S. Pat. No. 3,622,603, U.S. Pat. No. 3,482,971, EP-284 130].

WO 90/09 787 dicloses sulphonamides as radio- or chemosensitizing agents and their use in the treatment of tumours.

In addition, the compound N-[4-[[[5-(dimethylamino)-1-naphthalenyl]sulphonyl]-amino]phenyl]acetamide is known (J. Inst. Chem. (India) (1976), 48, Pt 6, 280–5).

The invention relates to compounds of the general formula (I)

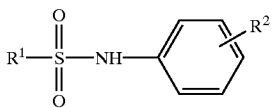

(I)

in which
R$^1$ represents a group which is selected from the following formulae

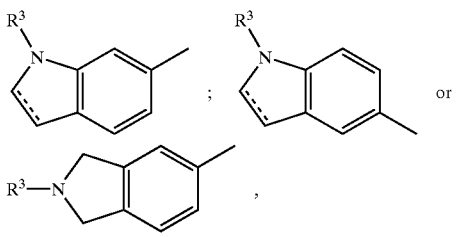

in which
---- represents a single or double bond,
R$^3$ represents hydrogen, (C$_1$–C$_6$)alkyl or (C$_3$–C$_6$)cycloalkyl, each of which may be substituted by 1 to 3 substituents selected from the group consisting of hydroxyl, halogen, amino, mono- or di(C$_1$–C$_6$)-alkylamino, (C$_1$–C$_6$)alkanoylamino, (C$_1$–C6) alkanoyloxy, (C$_1$–C$_6$)alkanoyl, carboxyl, (C$_1$–C$_6$) alkoxycarbonyl, carbamoyl, mono- or di(C$_1$–C$_6$) alkylaminocarbonyl and cyano, or
R$^3$ represents (C$_6$–C$_{10}$)arylsulphonyl, (C$_6$–C$_{10}$) arylcarbonyl, the (C$_6$–C$_{10}$)aryl group of which in each case can be substituted by 1 to 3 substituents selected from the group consisting of halogen, (C$_1$–C$_3$)alkyl, carboxyl, (C$_1$–C$_3$)alkoxycarbonyl, carbamoyl, mono- or di(C$_1$–C$_6$)alkylaminocarbonyl, cyano, hydroxyl and (C$_1$–C$_3$)alkoxy, or
R$^3$ represents (C$_1$–C$_6$)alkanoyl, (C$_1$–C$_6$)alkylsulphonyl, (C$_3$–C$_6$)cycloalkylcarbonyl, camphorsulphonyl or (C$_3$–C$_6$)cycloalkylsulphonyl, or
R$^3$ represents R$^4$—X—CO— or R$^4$—X—CS— in which X represents O, S, NR$^5$ in which R$^5$ represents hydrogen or (C$_1$–C$_3$)alkyl, and R$^4$ represents (C$_1$–C$_6$)alkyl, (C$_3$–C$_6$)cycloalkyl, (C$_6$–C$_{10}$)aryl or 5- to 10-membered heteroaryl, and
R$^2$ represents

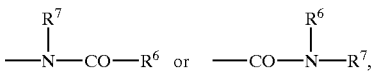

in which
R$^6$ is (C$_2$–C$_6$)alkenyl or (C$_1$–C$_8$)alkyl which is optionally substituted once to three times, identically or differently, by amino, protected amino, (C$_1$–C$_4$) alkylamino, hydroxyl, cyano, halogen, azido, nitro, trifluoromethyl, carboxyl or phenyl, where phenyl in turn can be substituted up to twice, identically or differently, by nitro, halogen, hydroxyl, (C$_1$–C$_4$) alkyl or (C$_1$–C$_4$)alkoxy, or
R$^6$ represents radicals of the formulae

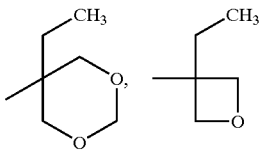

or
r—L—O—LO—Q,
in which
L represents a straight-chain or branched alkanediyl group with up to 6 carbon atoms,
Q represents (C$_1$–C$_6$)alkyl which is optionally substituted by carboxyl, or
represents radicals of the formulae

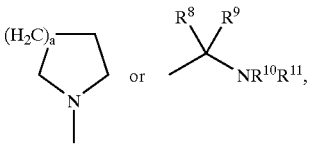

in which
a denotes the number 1 or 2,
R$^8$ denotes hydrogen,
R$^9$ denotes (C$_3$–C$_8$)cycloalkyl, (C$_6$–C$_{10}$)aryl or hydrogen, or denotes (C$_1$–C$_8$)alkyl,
where the (C$_1$–C$_8$)alkyl is optionally substituted by cyano, methylthio, hydroxyl, mercapto, guanidyl or by a group of the formula —NR$^{12}$R$^{13}$ or R$^{14}$—OC—,
in which
R$^{12}$ and R$^{13}$ denote, independently of one another, hydrogen, (C$_1$–C$_8$)alkyl or phenyl, and
R$^{14}$ denotes hydroxyl, benzyloxyl, (C$_1$–C$_6$) alkoxy or the abovementioned group —NR$^{12}$R$^{13}$,
or the (C$_1$–C$_8$)alkyl is optionally substituted by (C$_3$–C$_8$)-cycloalkyl or by (C$_6$–C$_{10}$)aryl which is in turn substituted by hydroxyl, halogen, nitro, (C$_1$–C$_8$)alkoxy or by the group —NR$^{12}$R$^{13}$,
in which R$^{12}$ and R$^{13}$ have the meaning indicated above,
or the (C$_1$–C$_8$)alkyl is optionally substituted by a 5- to 6-membered nitrogen-containing heterocycle or by indolyl, in which the corresponding —NH functions are optionally substituted by $(C_1-C_6)$alkyl or are protected by an amino protective group, $R^{10}$ and $R^{11}$ are identical or different and denote hydrogen or an amino protective group, $R^7$ represents hydrogen or represents a radical of the formula

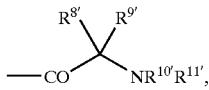

in which $R^{8'}$, $R^{9'}$, $R^{10'}$ and $R^{11'}$ have the meaning indicated above for $R^8$, $R^9$, $R^{10}$ and $R^{11}$ and are identical to or different from the latter, and the salts thereof.

The substances according to the invention may also be in the form of salts. Physiologically acceptable salts are preferred for the purposes of the invention.

Physiologically acceptable salts may be salts of the compounds according to the invention with inorganic or organic acids. Preference is given to salts with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Physiologically acceptable salts may likewise be metal or ammonium salts of the compounds according to the invention. Particularly preferred examples are sodium, potassium, magnesium or calcium salts, and ammonium salts derived from ammonia or organic amines such as, for example, ethylamine, di- or triethylamine, di- or triethanolamine, dicyclohexylamine, dimethylaminoethanol, arginine, lysine, ethylenediamine or 2-phenylethylamine.

The compounds in accordance with the invention of the general formula (1) may occur in various stereochemical forms which either are related as image and mirror image (enantiomers) or are not related as image and mirror image (diastereomers). The invention relates both to the antipodes and to the racemic forms, and the mixtures of diastereomers. The racemic forms can, just like the diastereomers, be separated into the stereoisomerically homogeneous components in a known manner.

In addition, certain compounds may exist in tautomeric forms. This is known to the skilled person, and the scope of the invention likewise encompasses such compounds.

$(C_1-C_6)$Alkyl generally represents for the purposes of the invention straight-chain or branched hydrocarbon radicals with 1 to 6 carbon atoms. Correspondingly, $(C_1-C_4)$alkyl and $(C_1-C_3)$alkyl generally represent for the purposes of the invention straight-chain or branched hydrocarbon radicals with respectively 1 to 4 and 1 to 3 carbon atoms. Examples which may be mentioned are: methyl, ethyl, propyl, isopropyl, butyl, isobutyl, sec-butyl, tert-butyl, pentyl, isopentyl, hexyl and isohexyl.

$(C_3-C_6)$Cycloalkyl represents cycloalkyl group with 3 to 6 carbon atoms and includes, for example: cyclopropyl, cyclopentyl and cyclohexyl. Cyclopropyl is preferred.

The $(C_1-C_6)$alkoxy group used in the present invention and also used in the definitions of $(C_1-C_6)$alkoxycarbonyl includes, for example, straight-chain or branched alkoxy groups with 1 to 6 carbon atoms, particularly preferably alkoxy groups with 1 to 4 carbon atoms ($(C_1-C_4)$alkoxy), and more preferably alkoxy groups with 1 to 3 carbon atoms ($(C_1-C_3)$alkoxy). Examples which may be mentioned are methoxy, ethoxy, propoxy, isopropoxy, butoxy, isobutoxy, pentoxy, isopentoxy, hexoxy and isohexoxy. Methoxy, ethoxy and propoxy are preferred.

Mono- or di$(C_1-C_6)$alkylamino includes for the purposes of the invention those whose alkyl groups have 1 to 6 carbon atoms. The alkylamino groups in this connection may be symmetrical or nonsymmetrical, such as, for example, dimethylamino, diethylamino, methylethylamino etc. This also applies to the mono- or di$(C_1-C_6)$alkylamino moiety in the mono- or di$(C_1-C_6)$alkylaminocarbonyl group.

$(C_6-C_{10})$Aryl represents for the purposes of the invention an aromatic radical with 6 to 10 carbon atoms. Preferred aryl radicals are phenyl and naphthyl.

5- to 10-membered heteroaryl represents for the purposes of the invention 5- to 10-membered heteroatom-containing rings which may contain in the ring 1 to 8 heteroatoms which are selected from O, S and N and include, for example, a pyridyl, furyl, thienyl, pyrrolyl, imidazolyl, oxazolyl, thiazolyl, isoxazolyl, triazolyl, thiadiazolyl, pyridazinyl, pyrazinyl, pyrimidinyl, indolizinyl, indolyl, benzo[b]thienyl, benzimidazolyl, pyridoimidazolyl, indazolyl, quinolyl, isoquinolyl, naphthyridinyl, quinazolinyl, etc.

5- to 6-membered nitrogen-containing heterocycles include, for example: pyrrolidine, piperidine, piperazine, morpholine, pyridyl, furyl, thienyl, pyrrolyl, imidazolyl, pyrazolyl, pyrazinyl, pyrimidinyl, pyridazinyl, etc.

Halogen includes for the purposes of the invention fluorine, chlorine, bromine and iodine. Chlorine or fluorine is preferred.

Concerning $(C_6-C_{10})$arylsulphonyl and -carbonyl, reference may be made to the definitions mentioned above for $(C_6-C_{10})$aryl.

$(C_1-C_6)$Alkanoyl, and $(C_1-C_6)$alkanoyl in the definition of $(C_1-C_6)$alkanoyloxy and $(C_1-C_6)$alkanoylamino, represents for the purposes of the invention straight-chain or branched alkanoyl with 1 to 6 carbon atoms. Examples which may be mentioned are: formyl, acetyl, propanoyl, butanoyl, pentanoyl, pivaloyl and hexanoyl.

The "alkanediyl group with up to 6 carbon atoms" designates in this connection straight-chain or branched hydrocarbon groups linked at two positions to other radicals. Examples of alkanediyl groups are: —$CH_2$—$CH_2$—, —$CH_2$—$CH_2$—$CH_2$—, —$C(CH_3)_2$—$CH_2$—, —$CH(CH_3)$—$CH_2$—, —$C(CH_3)_2$—$CH_2$—$CH_2$—, —$CH(CH_3)$—$CH_2$—$CH_2$—etc.

Amino protective groups for the purposes of the invention are the conventional amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tertbutoxycarbonyl, menthyloxycarbonyl, phenoxycarbonyl, 4-nitrophenoxycarbonyl, fluoroenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

In a preferred embodiment, the invention includes compounds of the formulae

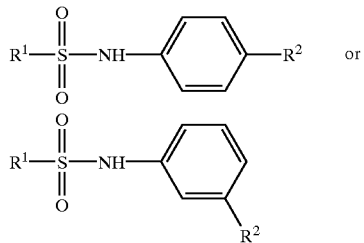

or in which $R^1$ and $R^2$ have the meaning indicated above.

In another preferred embodiment, the invention includes compounds of the general formula (I) in which:

$R^1$ represents a group selected from the formulae:

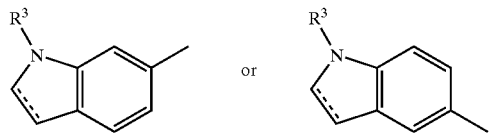

in which
---- represents a single or double bond, and
$R^3$ has the meaning indicated above, and the salts thereof.

In a preferred embodiment, the invention includes compounds of the general formula (I) in which:

$R^3$ represents hydrogen, $(C_1-C_6)$alkyl or $(C_1-C_6)$ alkanoyl, and $R^2$ represents

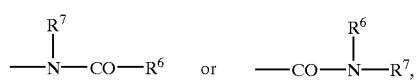

in which
$R^6$ is $(C_1-C_8)$alkyl, which is optionally substituted by halogen or hydroxyl, and
$R^7$ is hydrogen, and the salts thereof.

In a preferred embodiment, the invention includes compounds of the general formula (I) in which R is tert-butyl which is optionally substituted by halogen or hydroxyl, and the salts thereof.

The invention furthermore relates to processes for preparing the compounds of the formula (I).

In process (A), compounds of the general formula (II)

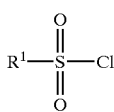

(II)

in which $R^1$ is as defined above, are reacted with compounds of the general formula (III)

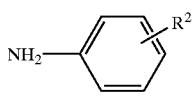

(III)

in which $R^2$ is as defined above, to give compounds of the general formula (I).

The reaction is preferably carried out in the presence of bases such as pyridine, triethylamine and Hünig base etc.

The reaction is preferably carried out in a solvent such as tetrahydrofuran, 1,4-dioxane, dichloromethane, etc.

The reaction is preferably carried out in a temperature range from −10° C. to 70° C.

The reaction is preferably carried out at atmospheric pressure.

In process (B), compounds of the general formula (Ia):

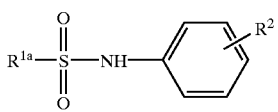

(Ia)

in which $R^2$ is, as defined above, and
$R^{1a}$ represents a group selected from the following formulae:

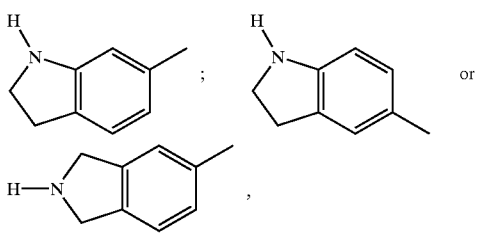

are reacted with compounds of the formula (IV):

(IV)

in which $R^3$ is as defined above, and A is a conventional leaving group, in a manner known per se in the presence of a base to give compounds of the general formula (Ib):

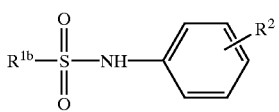

(Ib)

in which $R^2$ is as defined above, and $R^{1b}$ represents a group selected from the following formulae:

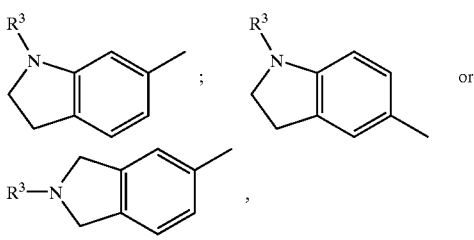

in which $R^3$ is as defined above.

A in this case represents a conventional leaving group used in nucleophilic substitution reactions, such as, for example, halogen (for example chlorine, bromine, iodine), OTs (Ts=tosyl) and OMes (Mes=mesyl).

Bases preferred in the reaction are tertiary amines such as pyridine, Hünig base etc., alkali metal hydroxide and alkali metal carbonate.

The reaction is preferably carried out in an inert solvent such as tetrahydrofuran, 1,4-dioxane, dichloromethane, dimethylformamide etc.

The reaction is preferably carried out in a temperature range from –10° C. to 100° C.

The reaction is preferably carried out under atmospheric pressure.

In process (C), compounds of the general formula (Ic)

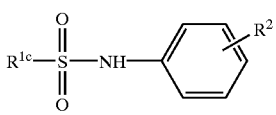

(Ic)

in which $R^2$ is as defined above, and $R^{1c}$ represents a group selected from the following formulae:

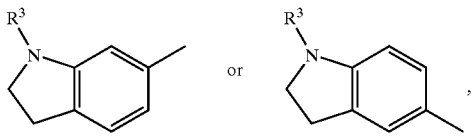

in which $R^3$ is as defined above, are converted by oxidation with DDQ (2,3-dichloro-5,6-dicyano-para-benzoquinone) in a manner known per se into compounds of the general formula (Id):

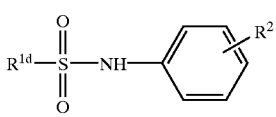

(Id)

in which $R^2$ is as defined above, $R^{1d}$ represents a group selected from the following formulae:

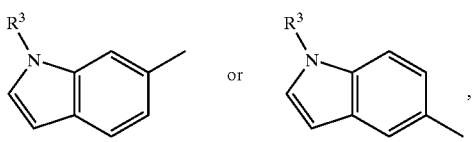

in which $R^3$ is as defined above.

The reaction is preferably carried out in a solvent such as 1,4-dioxane or 1,2-dichloroethane.

The reaction is preferably carried out in a temperature range from room temperature to the boiling point of the particular solvent under atmospheric pressure.

The reaction is preferably carried out under atmospheric pressure.

In process (D), compounds of the general formula (Ie)

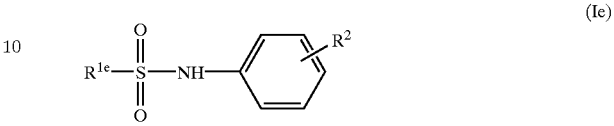

(Ie)

in which $R^2$ is as defined above, and $R^{1e}$ has the following formulae:

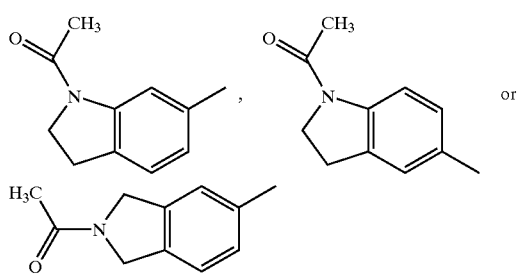

are reacted in a manner known per se in the presence of water with alkali metal hydroxides to give compounds of the formula (Ia).

Alkali metal hydroxides include in this case, for example, lithium hydroxide, sodium hydroxide, potassium hydroxide etc., and lithium hydroxide is preferred.

The reaction is preferably carried out in homogeneous aqueous solvent systems.

The reaction is preferably carried out in a temperature range from room temperature to 70° C.

The reaction is preferably carried out under atmospheric pressure

In process (E), compounds of the general formula (If)

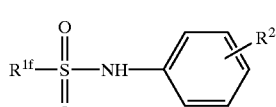

(If)

in which $R^2$ is as defined above, and $R^{1f}$ has the following formulae:

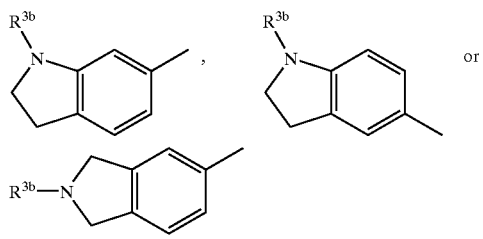

in which $R^{3b}$ represents $(C_1–C_6)$alkanoyl, are reacted in a manner known per se with complex metal hydrides to give compounds of the general formula (Ig):

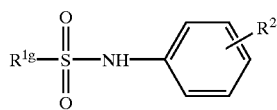

in which $R^2$ is as defined above and $R^{1g}$ has the following formulae:

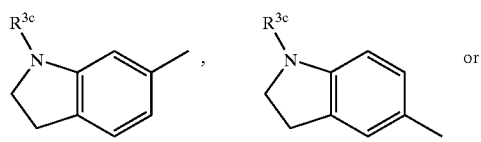

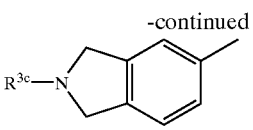

in which $R^{3c}$ represents $(C_1-C_6)$alkyl.

Complex metal hydrides preferably used in the reaction are lithium aluminium hydride, diisobutylaluminium hydride, etc.

The reaction is preferably out in a solvent such as tetrahydrofuran, 1,4-dioxane etc.

The reaction is preferably carried out in a temperature range from −50° C. to 40° C.

The reaction is preferably carried out under atmospheric pressure.

The processes according to the invention can be illustrated by the following reaction diagrams.

The indole and indoline compounds can be prepared as follows:

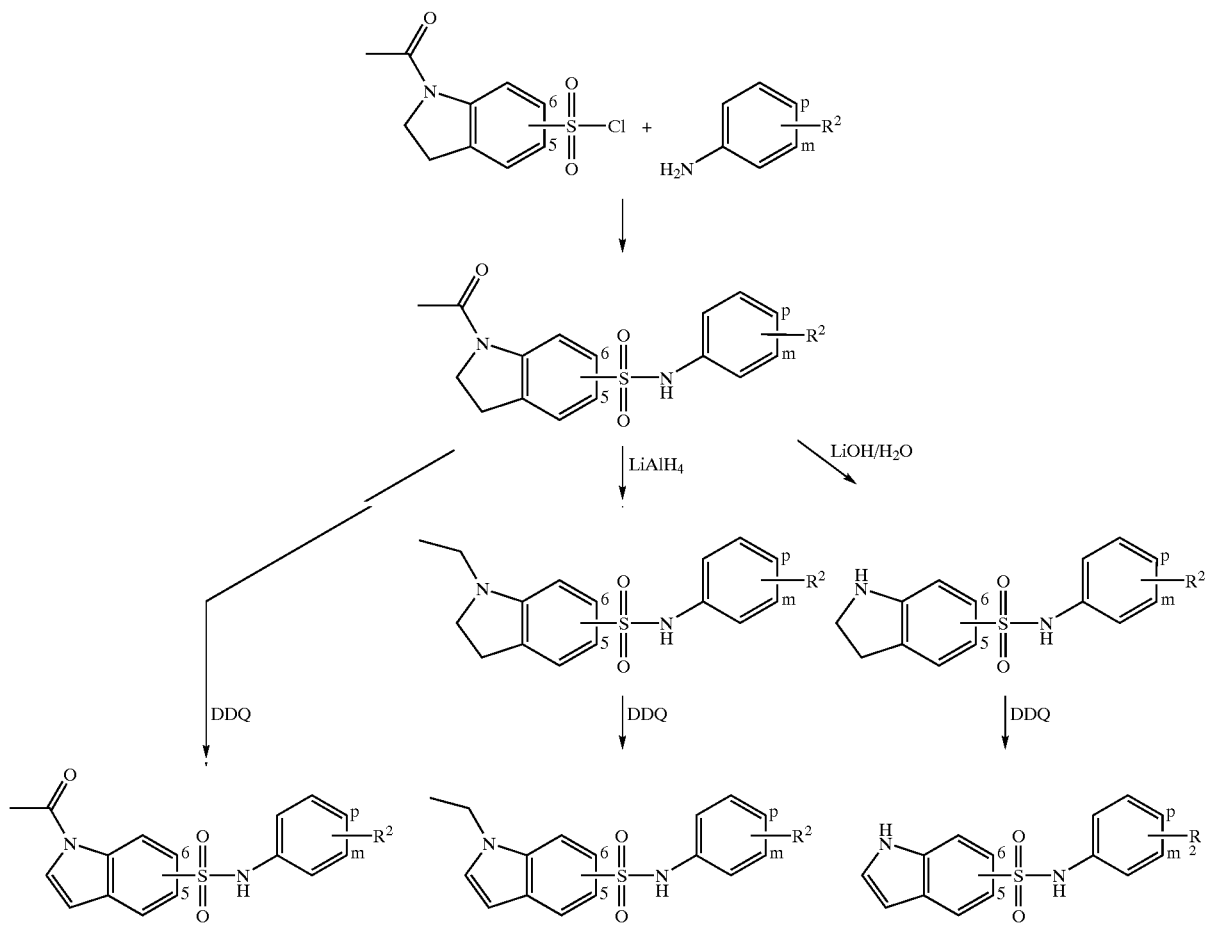

The compounds of the general formula (I) can then be obtained as described above from the unsubstituted indole and indoline compounds ($R^3$=hydrogen) by reaction with $R^3$—A.

The isoindoline compounds can be obtained, for example, as shown in the following diagram:

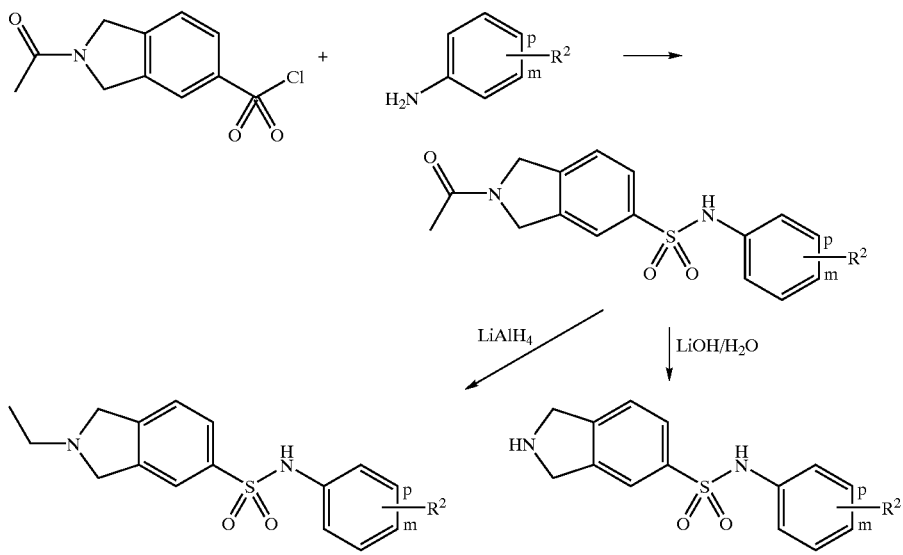

The compounds of the general formula (I) can then be obtained as described above from the unsubstituted isoindoline compounds ($R^3$=hydrogen) by reaction with $R^3$—A.

The preparation of the sulphonyl chloride starting compounds of the formula (II) is illustrated by the following reaction diagram:

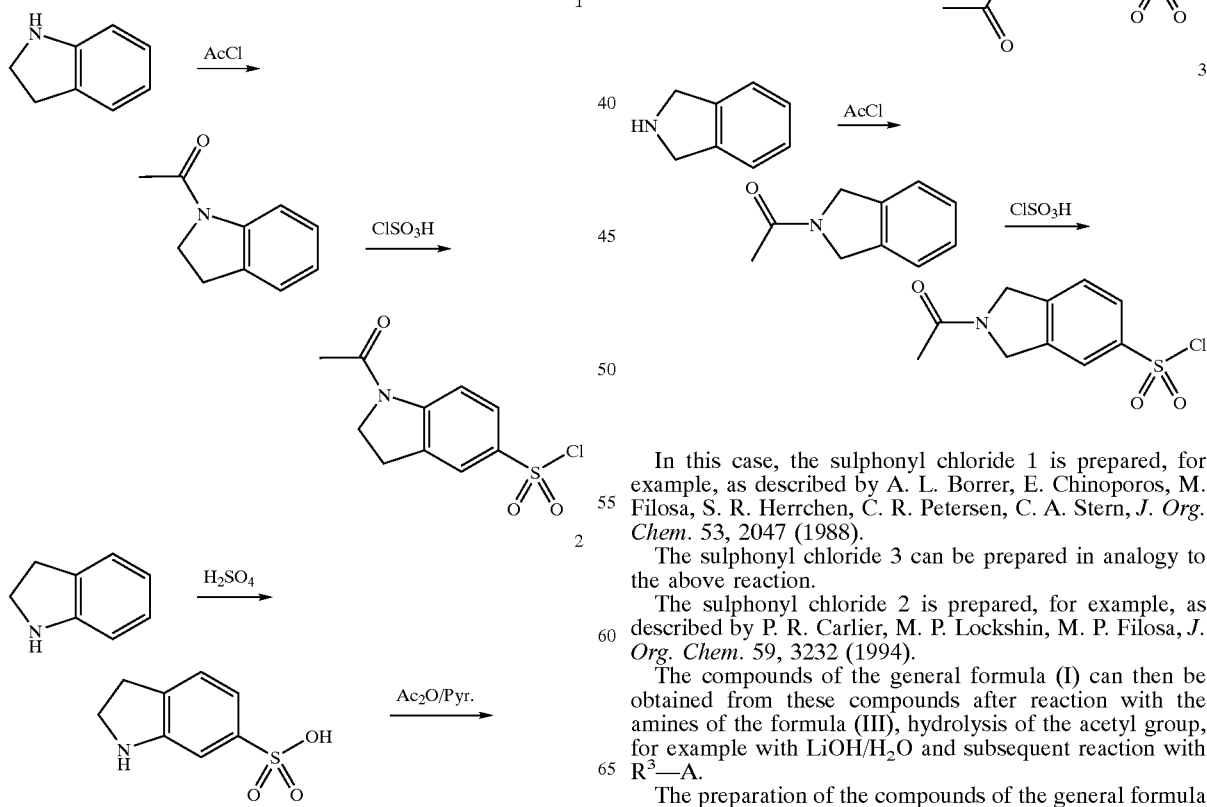

In this case, the sulphonyl chloride 1 is prepared, for example, as described by A. L. Borrer, E. Chinoporos, M. Filosa, S. R. Herrchen, C. R. Petersen, C. A. Stern, *J. Org. Chem.* 53, 2047 (1988).

The sulphonyl chloride 3 can be prepared in analogy to the above reaction.

The sulphonyl chloride 2 is prepared, for example, as described by P. R. Carlier, M. P. Lockshin, M. P. Filosa, *J. Org. Chem.* 59, 3232 (1994).

The compounds of the general formula (I) can then be obtained from these compounds after reaction with the amines of the formula (III), hydrolysis of the acetyl group, for example with $LiOH/H_2O$ and subsequent reaction with $R^3$—A.

The preparation of the compounds of the general formula (III) is illustrated for example in the following reaction diagram:

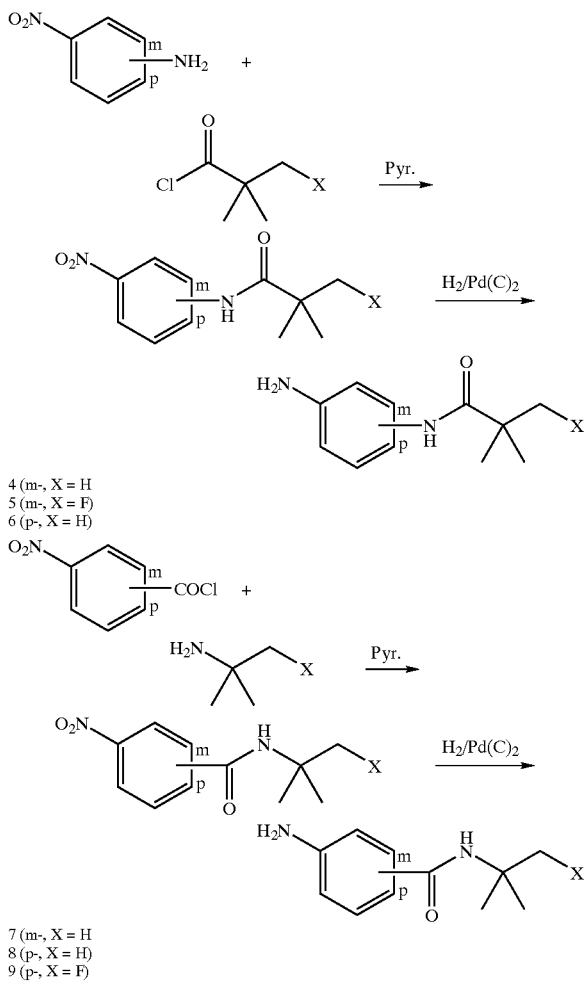

In this Pyr. means pyridine.

The aniline 4 is prepared, for example, as described in U.S. Pat. No. 3,979,202.

The aniline 6 is prepared, for example, as described by S. Rajappa, R. Sreenivasan, A. Khalwadekar, *J. Chem. Res. Miniprint* 5, 1657 (1986).

The aniline 7 is prepared, for example, as described in WO 96/31462.

The aniline 8 is prepared, for example, as described by R. W. Hartmann, M. Reichert, S. Goehring, *Eur. J. Med. Chem Chim. Ther.* 29, 807 (1994).

The anilines 5 and 9 are prepared in an analogous manner.

Concerning the exact reaction conditions, reference may be made to the examples and starting examples.

The invention further relates to. compounds of the formula (I) for use as pharmaceuticals.

The invention further relates to a pharmaceutical composition comprising a compound of the general formula (I) mixed with at least one pharmaceutically acceptable carrier or excipient.

The invention further relates to the use of the compounds of the general formula (I) for producing a pharmaceutical.

The invention further relates to the use of a compound of the general formula (I) for producing a pharmaceutical for the treatment of viral infections, in particular infections by cytomegaloviruses.

The compounds according to the invention of the general formula (I) show a surprising range of actions which could not have been predicted. They show an antiviral action on representatives of the group of Herpesviridae, in particular on human cytomegalovirus (HCMV). They are thus suitable for the treatment and prophylaxis of disorders caused by herpes viruses, in particular disorders caused by human cytomegalovirus (HCMV).

The anti-HCMV action was determined in a screening test system in 96-well microtitre plates with the assistance of human embryonic lung fibroblasts (HELF) cell cultures. The affect of these substances on the extent of the cytopathogenic effect was determined by comparison with the reference substance ganciclovir (Cymevene$^R$ sodium), a clinically approved anti-HCMV chemotherapeutic agent ($EC_{50}$, corresponding to the effective concentration at which a 50% inhibition of virus activity is achieved).

The substances dissolved (50 mM) in DMSO (dimethyl sulphoxide) are investigated on microtitre plates (96-well) in duplicate determinations (4 substances/plate). Toxic and cytostatic effects of the substances are also detected thereby ($CC_{50}$, corresponding to the concentration at which half the cells are destroyed owing to administration of the substance). After the appropriate substance dilutions (1:2) on the microtitre plate, a suspension of 50–100 HCMV-infected HELF cells and 30×105 uninfected HELF cells in Eagle's MEM with 10% fetal calf serum are put in each well, and the plates are incubated at 37° C. in a $CO_2$ incubator for several days.

After this time, the cell lawn in the virus controls free of substance, starting from 50–100 infectious centres, is completely destroyed by the cytopathogenic effect of the HCMV (100% CPE). After staining with Neutral Red and fixing with formalin/methanol, the plates are evaluated using a projection microscope (plaque viewer).

The results for two exemplary compounds are given below:

| Example | HCMV $EC_{50}$ $\mu$M | HELF $CC_{50}$ $\mu$M |
|---------|----------------------|----------------------|
| 1       | 0.055                | 15.6                 |
| 2       | 0.39                 | 86                   |

The compounds according to the invention thus represent valuable active substances for the treatment and prophylaxis of disorders caused by human cytomegalovirus. Examples of areas of indication which may be mentioned are:

1) Treatment and prophylaxis of HCMV infections in AIDS patients (retinitis, pneumonitis, gastrointestinal infections).

2) Treatment and prophylaxis of cytomegalovirus infections in bone marrow and organ transplant patients who often suffer life-threatening HCMV pneumonitis or encephalitis or gastrointestinal and systemic HCMV infections.

3) Treatment and prophylaxis of HCMV infections in neonates and in infants.

4) Treatment of an acute HCMV infection in pregnant women.

In Vivo Action

Animals:

5-week old male mice, strain NOD/LtSz-Prkdc(scid)/J, were purchased from a commercial breeder, (The Jackson Lab., Bar Harbor). The animals were kept under sterile conditions (including bedding and feed) in isolators.

Virus/Infection

Murine cytomegalovirus (MCMV), Smith strain, was passaged in vivo (BALB/c) and purified by fractional centrifugation. The titre was investigated using a plaque assay on primary embryonic mouse fibroblasts. The mice were infected intraperitoneally with a dose of $5\times10^5$ pfu in a total volume of 0.2 ml. This dose leads to death of 100% of the infected animals after about 11 days.

Treatment/Evaluation 24 hours after the infection, the mice were treated orally with substance twice a day (morning and evening) for a period of 8 days. The dose was 25 mg/kg of body weight, and the volume administered was 10 ml/kg of body weight. The substances were formulated as a 0.5% strength Tylose suspension. 16 hours after the last administration of substance, the animals were sacrificed painlessly and the salivary gland, liver and kidney were removed.

Genomic DNA was purified by phenol/chloroform extraction from 25 mg of the tissues. The DNA was quantified by photometry using the formula $OD_{260}\times 50$=mg/ml.

The purity of the DNA was checked by the $OD_{260}/OD_{280}$ ratio, and the DNA was then adjusted to pH=8.0 with tris-EDTA.

The MCMV DNA was quantified by DNA dot-blot hybridization. The probe used was a digoxygenin-labelled (Boehringer-Mannheim, likewise buffers mentioned unless otherwise described) 1.2 kb fragment from the MCMV, Smith, HindIII J, region. The signals were detected by chemiluminescence. For this purpose, the membrane was washed in 1× digoxygenin washing buffer 1 for 3 minutes. The filters were then incubated in 1× digoxygenin blocking solution, shaking at room temperature for 30 minutes. The filters were subsequently incubated in 20 ml/100 cm² of membrane with the anti-DIG-alkaline phosphatase conjugate solution (1:20000 in 1× digoxygenin blocking solution) for 30 minutes. This was followed by 2 washing steps each lasting 15 minutes with 1× digoxygenin washing buffer. The filters were then equilibrated in 1× digoxygenin detection buffer for 5 minutes, and detection took place with 1 ml/100 cm² area of membrane CDP-Star solution diluted 1:100. Spreading of the CDP-Star solution and incubation in a dark box for 5 minutes were followed by detection of the chemiluminescence or evaluation using an X-ray film (Kodak) or LumiImage (Boehringer Mannheim). All the results were statistically confirmed (analysis of variance using Statistica; StatSoft Inc.).

The novel active substances can be composed in a known manner into conventional formulations such as tablets, coated tablets, pills, granules, aerosols, syrups, emulsions, suspensions and solutions by use of inert, nontoxic, pharmaceutically suitable carriers or solvents. The therapeutically active compound should in each case be present in a concentration of about 0.5 to 90% by weight of the complete mixture, that is to say in amounts sufficient to reach the dosage range indicated.

The formulations are produced, for example, by extending the active substances with solvents and/or carriers, where appropriate with use of emulsifiers and/or dispersants, and it is possible for example in the case where water is used as diluent where appropriate to use organic solvents as auxiliary solvents.

Administration takes place in a conventional way, preferably orally, parenterally or topically, in particular perlingually, intravenously or intravitally, where appropriate as depot in an implant.

In the case of parenteral use, solutions of the active substances can be employed using suitable liquid carrier materials.

It has generally proved advantageous on intravenous administration to administer amounts of about 0.001 to 10 mg/kg, preferably about 0.01 to 5 mg/kg, of body weight to achieve effective results, and the dose on oral administration is about 0.01 to 25 mg/kg, preferably 0.1 to 10 mg/kg, of body weight.

It may nevertheless be necessary where appropriate to deviate from the stated amounts, in particular as a function of the body weight and the type of the administration route, of the individual behaviour in relation to the medicament, the nature of its formulation and the time or interval over which administration takes place. Thus, in some cases it may be sufficient to make do with less than the aforementioned minimum amount, whereas in other cases the upper limit mentioned must be exceeded. In the event of administration of larger quantities, it may be advisable to divide these into several individual doses over the day.

It may, where appropriate, be worthwhile to combine the compounds according to the invention with other active substances.

EXAMPLES

Starting Compounds

A) Sulphonyl Chlorides

N-Acetylindoline-5-sulphonyl chloride was prepared by a literature method (A. L. Borrer, E. Chinoporos, M. Filosa, S. R. Herrchen, C. R. Petersen, C. A. Stern, *J. Org. Chem.* 53, 2047 (1988)) as was N-acetylindoline-6-sulphonyl chloride (P. R. Carlier, M. P. Lockshin, M. P. Filosa, *J. Org. Chem.* 59, 3232 (1994)). N-Acetylisoindoline-5-sulphonyl chloride was prepared from N-acetylisoindoline and chlorosulphonic acid in analogy to N-acetylindoline-5-sulphonyl chloride.

B) Anilines

The required anilines were prepared by literature methods (Monsanto, U.S. Pat. No. 3,979,202, S. Rajappa, R. Sreenivasan, A. Khalwadekar, *J. Chem. Res. Miniprint* 5, 1657 (1986), WO 96/31462, R. W. Hartmann, M. Reichert, S. Göring, *Eur. J. Med. Chem. Chim. Ther.* 29, 807 (1994)) as depicted in the above diagrams.

EXAMPLES

A) N-Acetyl(iso)indoline Sulphonamides

Example 26

N-(N-Acetylindoline-5-sulphonyl)-N'-(3-fluoro-2,2-di methylpropanoyl)-1,3-diamino-benzene A solution of 3.50 g (16.65 mmol) of N-(3-fluoro-2,2-dimethylpropanoyl)-1,3-diami-nobenzene in 10 ml of dry THF was added dropwise to a solution of 3.93 g (15.13 mmol) of N-acetylindoline-5-sulphonyl chloride and 5.99 g (75.67 mmol) of pyridine in 50 ml of dry THF at 0° C. The ice bath was removed, and the stirring was continued at room temperature for 24 hours. The solvent and excess pyridine were then removed in vacuo. The resulting suspension was treated with a mixture of 25 ml of ether, 5 ml of ethyl acetate and 2 molar aqueous hydrochloric acid. The crystalline product was isolated and washed successively with water and ether. 4.90 g (11,30 mmol, 75% yield) of pale pink-coloured solid were obtained.

$R_f$: 0.40 (ethyl acetate).

$^1$H-NMR (300 MHz, DMSO-$d_6$, δ/ppm): 10.09 (1H, s), 9.31 (1H, s), 8.07 (1H, d), 7.62 (1H, s), 7.61 (1H, d), 7.53 (1H, t), 7.24 (1H, dd), 7.11 (1H, t), 6.78 (1H, dd), 4.49 (2H, d), 4.11 (2H, t), 3.13 (2H, t), 2.13 (3H, s), 1.22 (6H, s). MS (ESI+, $CH_3CN/H_2O/CH_3CO_2H$, m/z): 434.2 (M+H$^+$).

The other N-acetylindoline- and isoindolinesulphonamides of Examples 25, 28, 32, 33, 18, 36, 56, 50, 49, 63, 61 and 59, as shown in the table below, were prepared in the same manner.

B) N-Ethyl(iso)indoline Sulphonamides

Example 19

N-(N-Ethylindoline-5-sulphonyl)-N'-(3-fluoro-2,2-dimethylpropanoyl)-1,3-diamino-benzene A solution of 1.0 g (2.31 mmol) of N-(N-acetylindoline-5-sulphonyl)-N'-(3-fluoro-2,2-dimethylpropanoyl)-1,3-diaminobenzene in 30 ml of dry THF was reacted with 2.80 ml (2.77 mmol) of a 1 molar solution of lithium aluminium hydride in THF at 0° C. The ice-water bath was removed and the stirring was continued at room temperature for 2 hours. The reaction was stopped by adding methanol. The mixture was diluted with ethyl acetate and washed successively with aqueous potassium sodium tartrate solution, aqueous (5% strength) sodium hydrogen phosphate solution, water and brine and dried over anhydrous sodium sulphate. The product was purified by preparative HPLC. 105 mg (0.25 mmol, 11% yield) of a white solid were obtained.

$R_f$: 0.17 (cyclohexane/ethyl acetate, 1:1). $^1$H-NMR (300 MHz, DMSO-$d_6$, δ/ppm): 9.87 (1H, s), 9.31 (1H, s), 7.51 (1H, t), 7.42 (1H, dd), 7.34 (1H, d), 7.23 (1H, dd), 7.10 (1H, t), 6.78 (1H, d), 4.49 (2H, d), 3.44 (2H, t), 3.17 (2H, quart.), 2.91 (2H, t), 1.05 (3H, t). MS (ESI+, $CH_3CN/H_2O/CH_3CO_2H$, m/z): 442 (M+Na$^+$), 420 (M+H$^+$).

The other N-ethylindoline- and isoindolinesulphonamides of Examples 15, 20, 35, 30, 34, 8, 11, 27, 46, 41, 40, 62, 60 and 57 in the following table were obtained in the same way.

C) (Iso)indolinesulphonamides

Example 16

4-[N-(5-Indolinesulphonyl)amino]-N-(tert.-butyl)benzamide 300 mg (0.72 mmol) of 4-[N-(N-acetylindoline-5-sulphonyl)amino]-N-(tert-butyl)benzamide were dissolved in 21 ml of aqueous (5% strength) lithium hydroxide solution. The mixture was kept at 60° C. for 24 hours. After cooling, aqueous (5% strength) sodium hydrogen phosphate solution was added. The aqueous layer was extracted with ethyl acetate. The combined organic extracts were washed successively with water and brine and dried over anhydrous sodium sulphate. The product was recrystallized from ether. 230 mg (0.62 mmol, yield 85%) of a white solid were obtained.

$R_f$: 0.56 (ethyl acetate).

$^1$H-NMR (400 MHz, DMSO-$d_6$, δ/ppm): 10.18 (1H, s), 7.63 (2H, d), 7.53 (1H, s), 7.36 (1H, d), 7.35 (1H, s), 7.08 (2H, d), 6.42 (1H, s), 6.41 (1H, d), 3.49 (2H, t), 2.93 (2H, t), 1.32 (9H, s). MS (CI, $NH_3$, m/z): 391 (M+$NH_4^+$), 374 (M+H$^+$).

The other indoline- and isoindolinesulphonamides of Examples 24, 38, 23, 37, 31, 55, 54, 53, 58, 65 and 64 in the following table were obtained in the same way.

D) N-Acetylindolesulphonamide

Example 2

4-[N-Acetylindole-5-sulphonylamino]-N-(tert-butyl)benzamide

A mixture of 200 mg (0.481 mmol) of 4-[N-acetylindoline-5-sulphonylamino]-N-(tert-butyl)benzamide and 164 mg (0.722 mmol) of DDQ in 10 ml of dry 1,4-dioxane was heated under reflux for 48 hours. 80 mg (0.352 mmol) portions of DDQ were added after 6 and 24 hours. The product was isolated by flash chromotography (silica gel, ethyl acetate/cyclohexane, 4:1). 85 mg (0.206 mmol, 42% yield) of a white solid were obtained.

$R_f$: 0.62 (ethyl acetate).

$^1$H-NMR (400 MHz, DMSO-d6, δ/ppm): 10.54 (1H, s), 8.43 (1H, d), 8.11 (1H, d), 8.01 (1H, d), 7.74 (1H, dd), 7.61 (2H, d), 7.53 (1H, s), 7.11 (2H, d), 6.88 (1H, d), 2.66 (3H, s), 1.30 (9H, s). MS (CI, $NH_3$, m/z): 431 (M+$NH_4^+$), 414 (M+H$^+$).

The other N-acetylindolesulphonamides of Examples 4, 7, 21, 29, 13, 43, 47 and 48 in the following table were obtained in the same way.

E) N-Ethylindolesulphonamides

Example 1

N-[(N-Ethylindole)-5-sulphonyl]-N'-(3-fluoro-2,2-dimethylpropanoyl)-1,3-diamino-benzene and 27 mg (0.25 mmol) of DDQ in 7 ml of dry 1,4-dioxane were heated under reflux for 3 hours. After evaporation of the solvent, the product was isolated by flash chromotography (silica gel, cyclohexane/ethyl acetate, 1:1). 55 mg (0.132 mmol, 79% yield) of a white solid were obtained.

$R_f$: 0.30 (cyclohexane/ethyl acetate, 1:1).

$^1$H-NMR (300 MHz, DMSO-$d_6$ δ/ppm): 10.08 (1H, s), 9.80 (1H, s), 8.07 (1H, d), 7.63–7.52 (4H, m), 7.21 (1H, d), 7.08 (1H, t), 6.81 (1H, d), 6.59 (1H, d), 4.48 (2H, d), 4.22 (2H, quart,), 1.32 (3H, t), 1.20 (6H, s). MS (CI, $NH_3$, m/z): 435 (M+$NH_4^+$), 418 (M+H$^+$).

The other N-ethylindolesulphonamides of Examples 9, 22, 3, 5, 10, 44, 51 and 45 in the following table were obtained in the same way.

F) Indolesulphonamides

Example 6

4-[N-(Indole-5-sulphonyl)amino]-N-(tert-butyl)benzamide

A mixture of 230 mg of 4-(indoline-5-sulphonylamino)-N-(tert-butyl)benzamide and 210 mg (0.924 mmol) of DDQ in 10 ml of dry 1,4-dioxane was heated under reflux for 4 hours. After evaporation of the solvent, the product was isolated by flash chromotography (silica gel, cyclohexane/ethyl acetate, 1:1). 78 mg (0.21 mmol, 34% yield) of a white solid were obtained.

$R_f$: 0.30 (dichloromethane/methanol, 100:5).

$^1$H-NMR (400 MHz, DMSO-$d_6$, δ/ppm): 10.58 (1H, s), 10.40 (1H, s), 8.08 (1H, s), 7.60 (2H, d), 7.52–7.50 (4H, m), 7.12 (2H, d), 6.60 (1H, d), 1.30 (9H, s). MS (CI, $NH_3$, m/z): 743 (2M+H$^+$), 389 (M+$NH_4^+$), 372 (M+H$^+$).

The other indolesulphonamides of Examples 12, 17, 42, 52 and 39 in the following table were obtained in the same way.

The following table shows Examples 1 to 65, their structural formulae and the $R_f$ values obtained.

| No. | Compound | Rf[a] |
|---|---|---|
| 1 | 1-ethyl-1H-indole-5-sulfonyl-NH-(3-(NH-C(O)-C(CH3)2-CH2F)-phenyl) | 0.30 (B) |
| 2 | 1-acetyl-1H-indole-5-sulfonyl-NH-(4-(C(O)-NH-C(CH3)3)-phenyl) | 0.62 (A) |
| 3 | 1-ethyl-1H-indole-5-sulfonyl-NH-(4-(C(O)-NH-C(CH3)3)-phenyl) | 0.29 (B) |
| 4 | 1-acetyl-1H-indole-5-sulfonyl-NH-(3-(NH-C(O)-C(CH3)3)-phenyl) | 0.63 (A) |
| 5 | 1-ethyl-1H-indole-5-sulfonyl-NH-(4-(C(O)-NH-C(CH3)2-CH2F)-phenyl) | 0.26 (B) |

-continued
| | | |
|---|---|---|
| 6 | 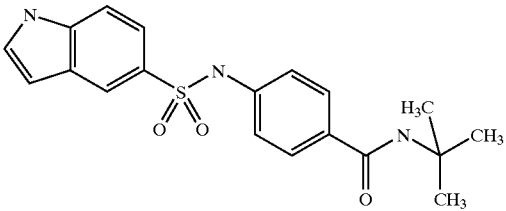 | 0.30 (D) |
| 7 | 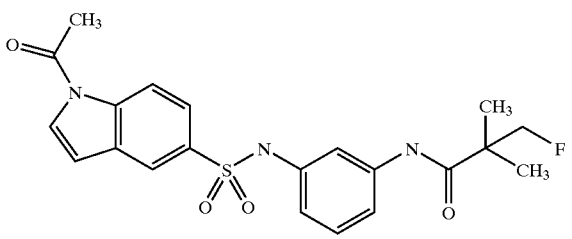 | 0.66 (A) |
| 8 | 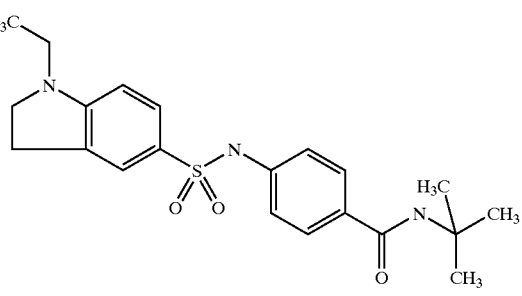 | 0.63 (A) |
| 9 | 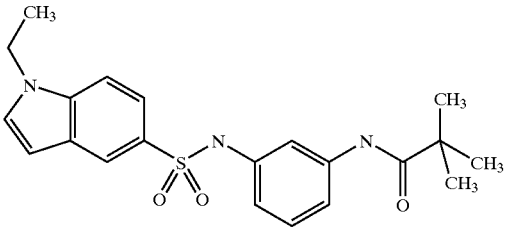 | 0.38 (B) |
| 10 | 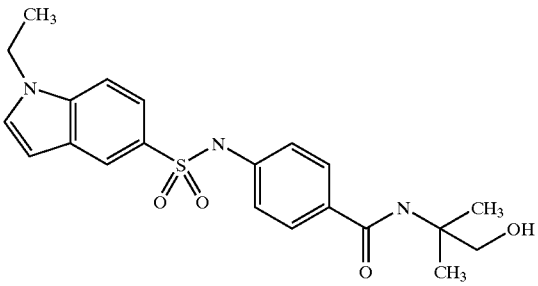 | 0.05 (B) |
| 11 | 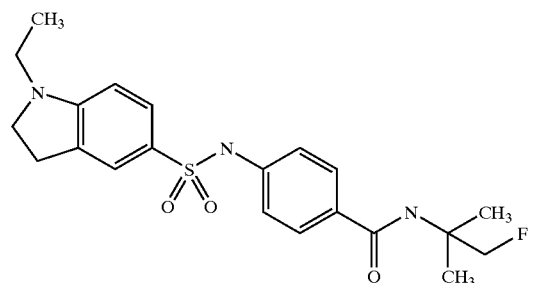 | 0.33 (B) |

-continued
| | | |
|---|---|---|
| 12 | 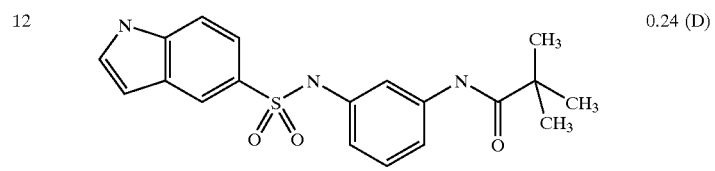 | 0.24 (D) |
| 13 | 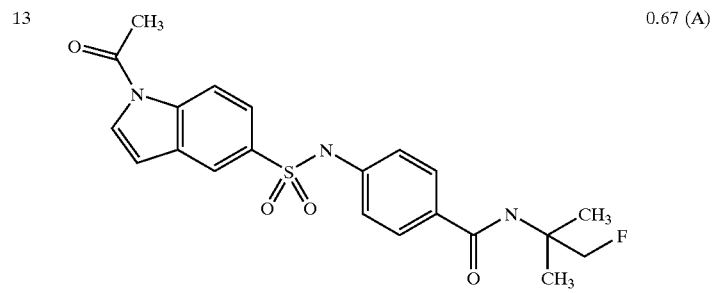 | 0.67 (A) |
| 14 | 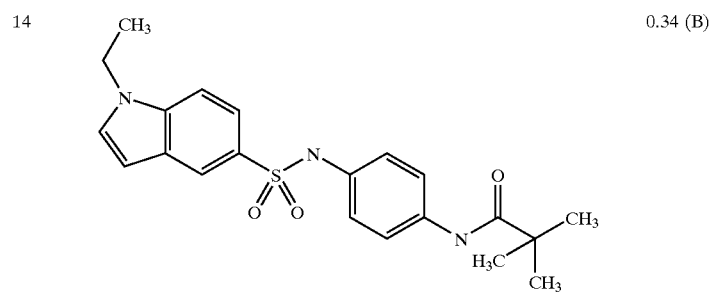 | 0.34 (B) |
| 15 | 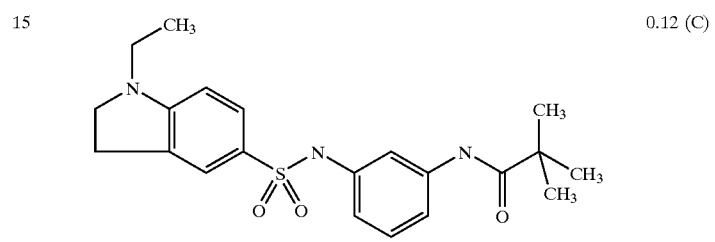 | 0.12 (C) |
| 16 | 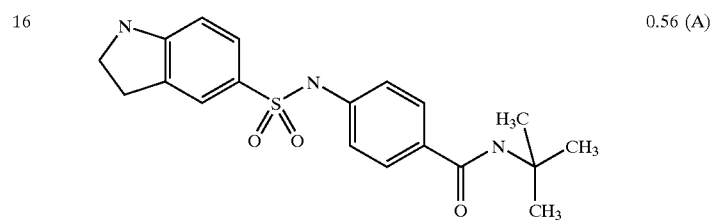 | 0.56 (A) |
| 17 | 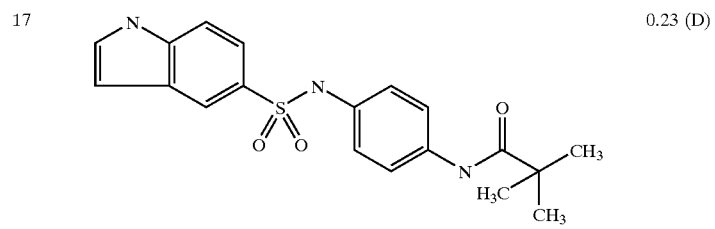 | 0.23 (D) |

-continued
| | | |
|---|---|---|
| 18 | 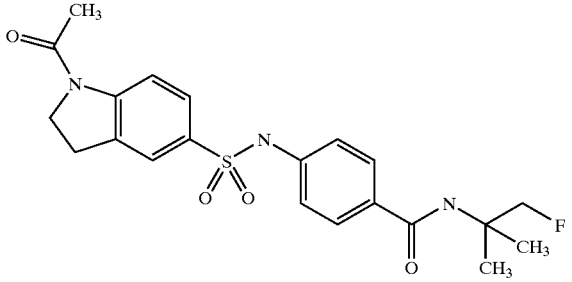 | 0.35 (A) |
| 19 | 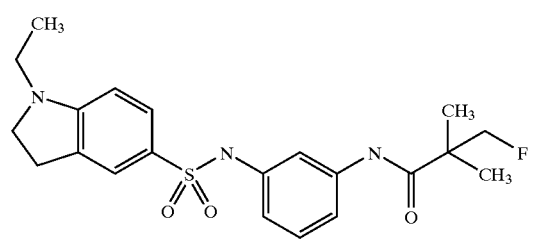 | 0.17 (B) |
| 20 | 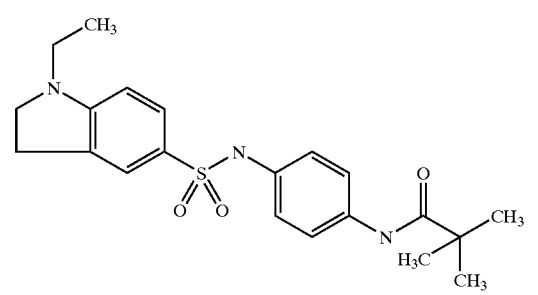 | 0.66 (D) |
| 21 | 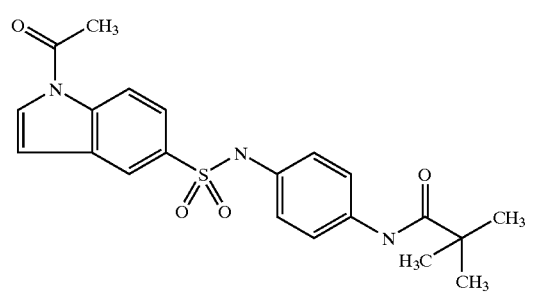 | 0.34 (D) |
| 22 | 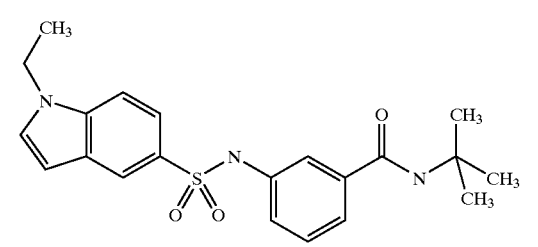 | 0.29 (B) |
| 23 | 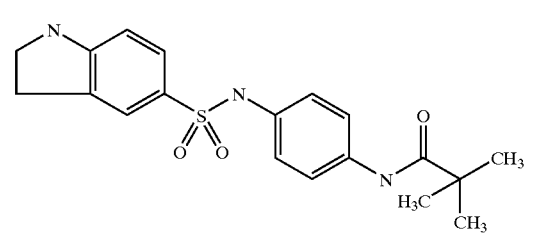 | 0.58 (A) |

-continued
| | | |
|---|---|---|
| 24 | 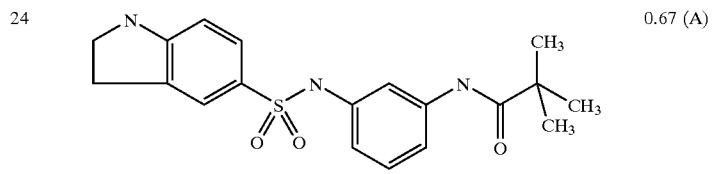 | 0.67 (A) |
| 25 | 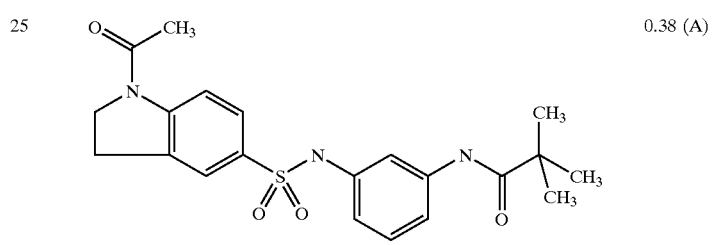 | 0.38 (A) |
| 26 | 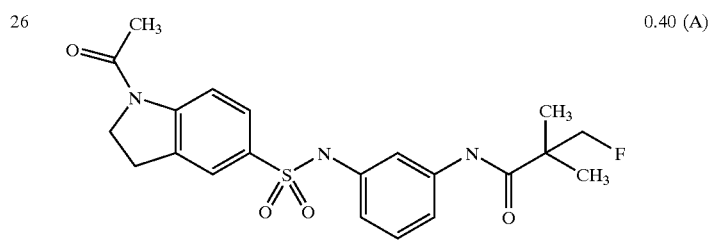 | 0.40 (A) |
| 27 | 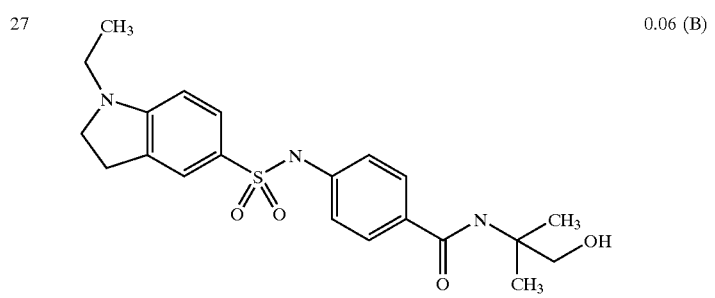 | 0.06 (B) |
| 28 | 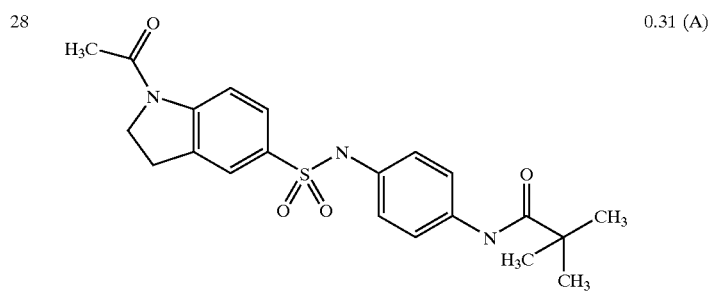 | 0.31 (A) |
| 29 | 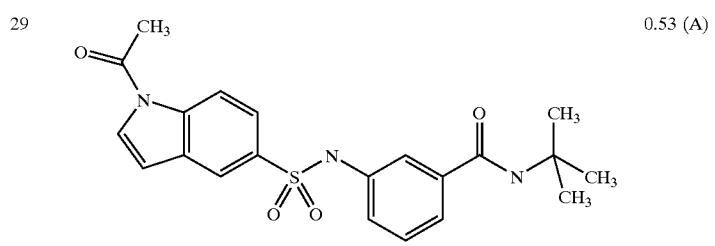 | 0.53 (A) |

-continued
| | | |
|---|---|---|
| 30 | 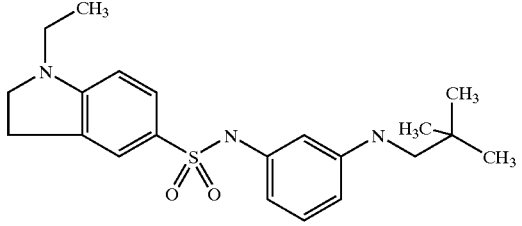 | 0.36 (C) |
| 31 | 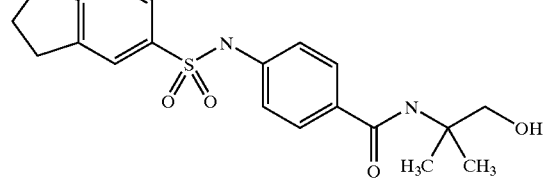 | 0.32 (A) |
| 32 | 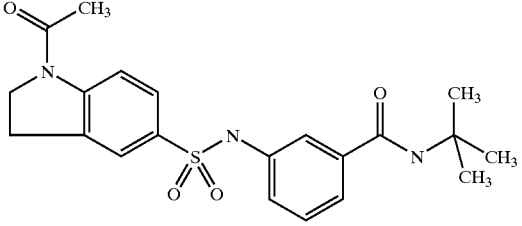 | 0.33 (A) |
| 33 | 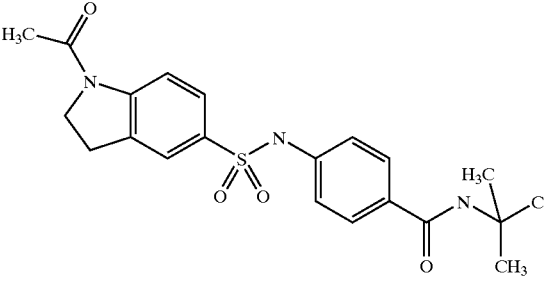 | 0.16 (B) |
| 34 | 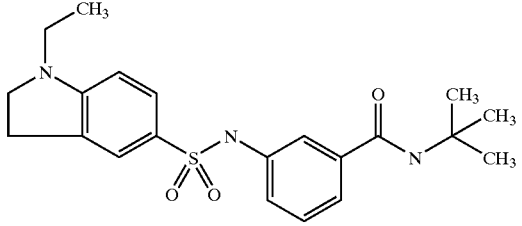 | 0.71 (A) |
| 35 | 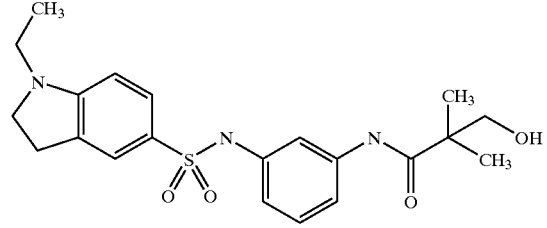 | 0.12 (C) |

-continued
| No. | Compound | $R_f^{[a]}$ |
|---|---|---|
| 36 | 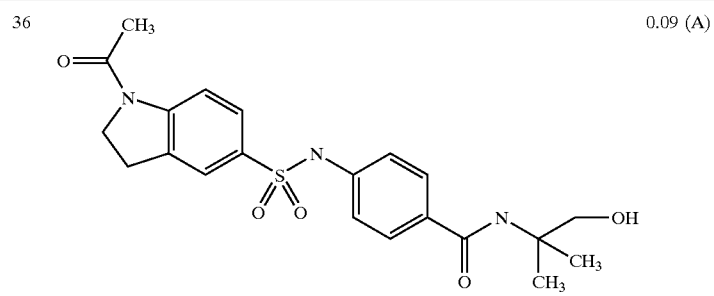 | 0.09 (A) |
| 37 | 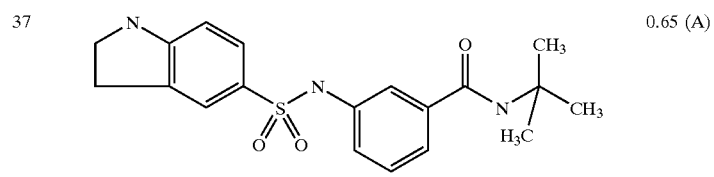 | 0.65 (A) |
| 38 | 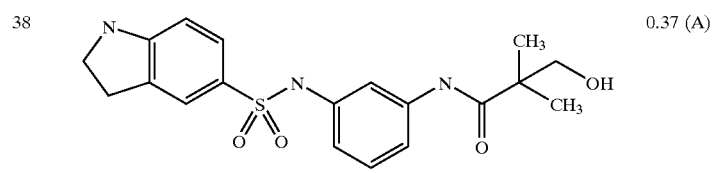 | 0.37 (A) |
| No. | Compound | $R_f^{[a]}$ |
|---|---|---|
| 39 | 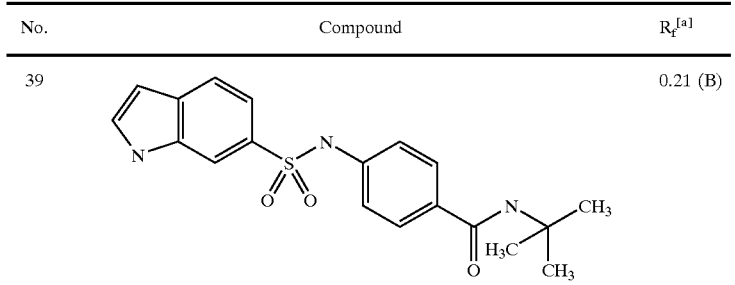 | 0.21 (B) |
| 40 | 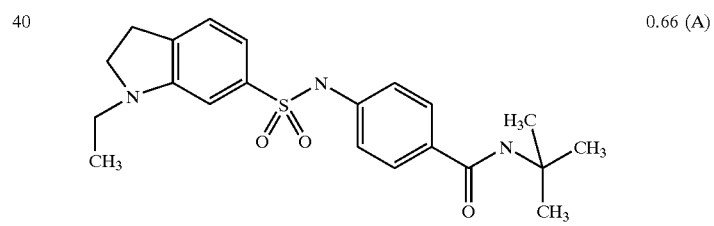 | 0.66 (A) |
| 41 | 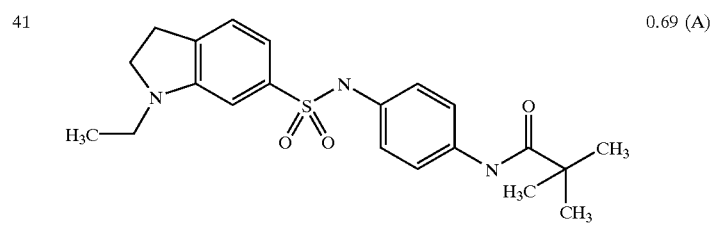 | 0.69 (A) |
| 42 | 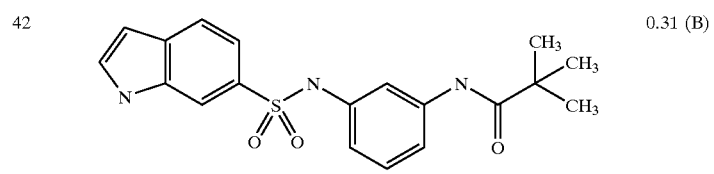 | 0.31 (B) |

-continued
| | | |
|---|---|---|
| 43 | 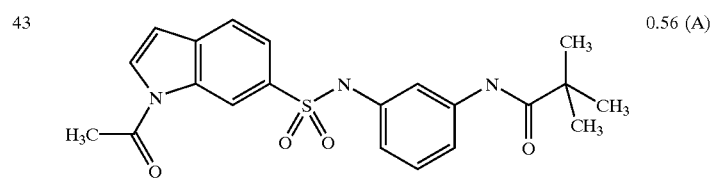 | 0.56 (A) |
| 44 | 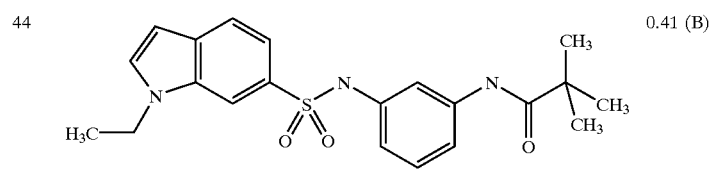 | 0.41 (B) |
| 45 | 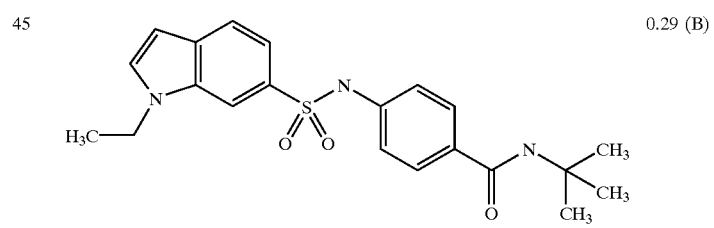 | 0.29 (B) |
| 46 | 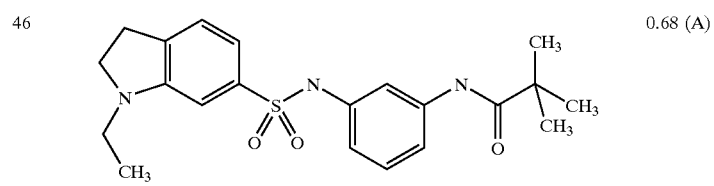 | 0.68 (A) |
| 47 | 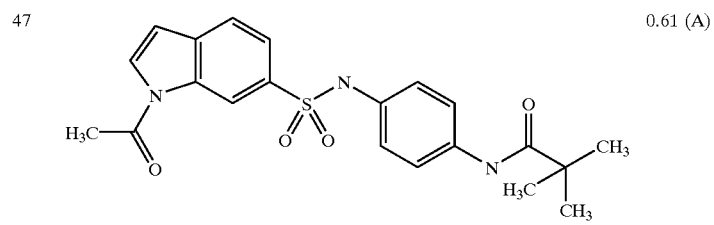 | 0.61 (A) |
| 48 | 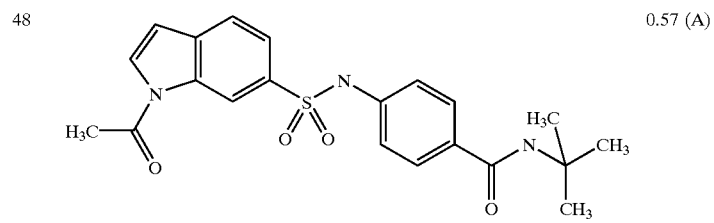 | 0.57 (A) |
| 49 | 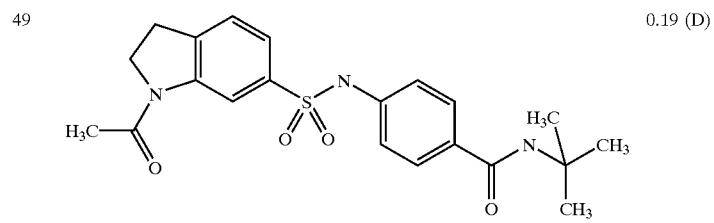 | 0.19 (D) |

-continued
| | | |
|---|---|---|
| 50 | 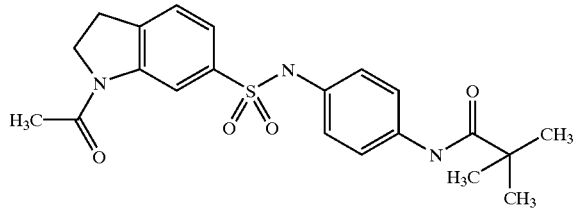 | 0.20 (D) |
| 51 | 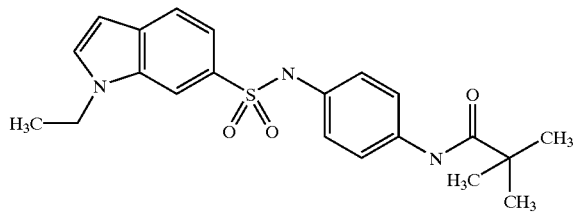 | 0.32 (B) |
| 52 | 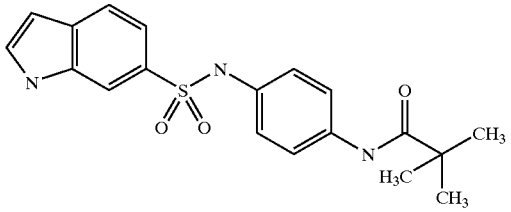 | 0.19 (B) |
| 53 | 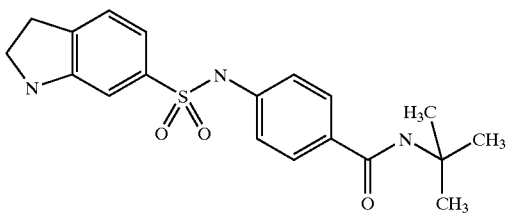 | 0.54 (A) |
| 54 | 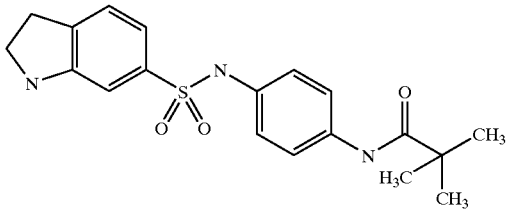 | 0.61 (A) |
| 55 | 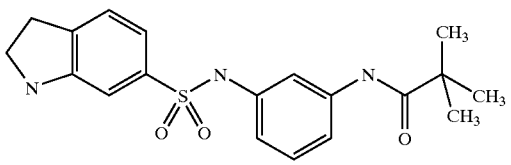 | 0.63 (A) |
| 56 | 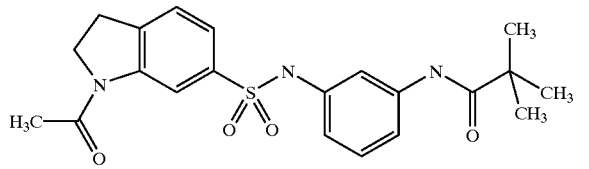 | 0.24 (D) |

-continued
| | | |
|---|---|---|
| 57 | 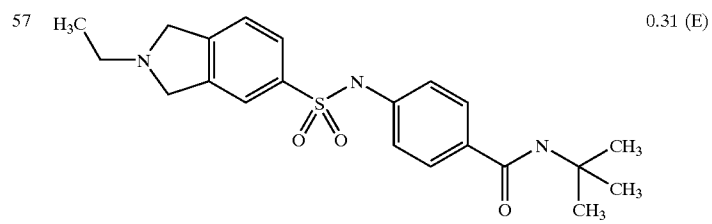 | 0.31 (E) |
| 58 | 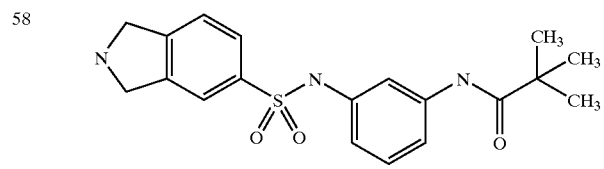 | |
| 59 | 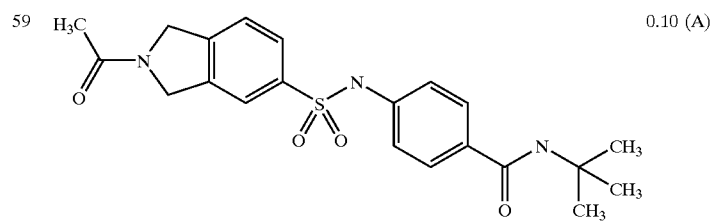 | 0.10 (A) |
| 60 | 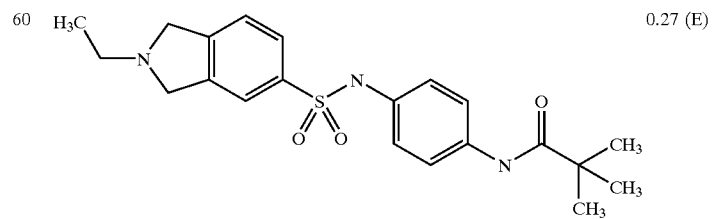 | 0.27 (E) |
| 61 | 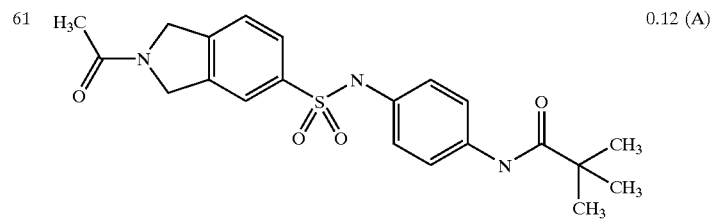 | 0.12 (A) |
| 62 | 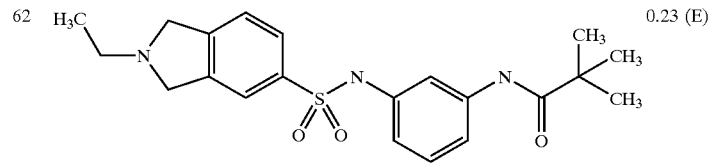 | 0.23 (E) |
| 63 | 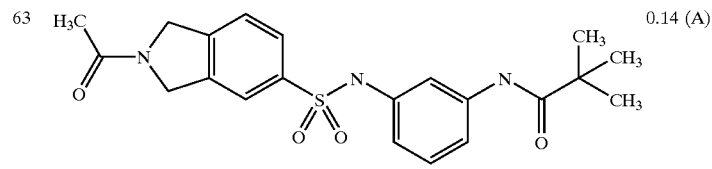 | 0.14 (A) |

[a] solvents:
A: ethyl acetate
B: cyclohexane/ethyl acetate (V/V = 1:1)
C: cyclohexane/ethyl acetate (V/V = 2:1)
D: dichloromethane/methanol (V/V = 100:1)
E: ethyl acetate/methanol (V/V - 4.1)
The group —N— as written in the formulae in the above table means that the group is saturated where appropriate by a hydrogen atom (—NH—).

What is claimed is:
1. Compounds of the general formula (I)

in which
$R^1$ represents a group which is selected from the following formulae in which
---- represents a single or double bond,
$R^3$ represents hydrogen, ($C_1$–$C_6$)alkyl or ($C_3$–$C_6$) cycloalkyl, each of which may be substituted by 1 to 3 substituents selected from the group consisting of hydroxyl, halogen, amino, mono- or di($C_1$–$C_6$)-alkylamino, ($C_1$–$C_6$)alkanoylamino, ($C_1$–$C_6$) alkanoyloxy, ($C_1$–$C_6$)alkanoyl, carboxyl, ($C_1$–$C_6$) alkoxycarbonyl, carbamoyl, mono- or di($C_1$–$C_6$) alkylaminocarbonyl and cyano, or
$R^3$ represents ($C_6$–$C_{10}$)arylsulphonyl, ($C_6$–$C_{10}$) arylcarbonyl, the ($C_6$–$C_{10}$)aryl group of which in each case can be substituted by 1 to 3 substituents selected from the group consisting of halogen, ($C_1$–$C_3$)alkyl, carboxyl, ($C_1$–$C_3$)alkoxycarbonyl, carbamoyl, mono- or di($C_1$–$C_6$)alkylaminocarbonyl, cyano, hydroxyl and ($C_1$–$C_3$)alkoxy, or
$R^3$ represents ($C_1$–$C_6$)alkanoyl, ($C_1$–$C_6$)alkylsulphonyl, ($C_3$–$C_6$)cycloalkylcarbonyl, camphorsulphonyl or ($C_3$–$C_6$)cycloalkylsulphonyl, or
$R^3$ represents $R^4$—X—CO— or $R^4$—X—CS— in which X represents O, S, $NR^5$ in which $R^5$ represents hydrogen or ($C_1$–$C_3$)alkyl, and
$R^4$ represents ($C_1$–$C_6$)alkyl, ($C_3$–$C_6$)cycloalkyl, ($C_6$–$C_{10}$)aryl or 5- to 10-membered heteroaryl, and
$R^2$ represents $$-\!-\!-\underset{\underset{R^7}{|}}{N}\!-\!CO\!-\!R^6 \quad \text{or} \quad -\!-\!-CO\!-\!\underset{\underset{R^7}{|}}{N}\!-\!R^6,$$

in which
$R^6$ is ($C_2$–$C_6$)alkenyl or ($C_1$–$C_8$)alkyl which is optionally substituted once to three times, identically or differently, by amino, protected amino, ($C_1$–$C_4$) alkylamino, hydroxyl, cyano, halogen, azido, nitro, trifluoromethyl, carboxyl or phenyl, where phenyl in turn can be substituted up to twice, identically or differently, by nitro, halogen, hydroxyl, ($C_1$–$C_4$) alkyl or ($C_1$–$C_4$)alkoxy, or
$R^6$ represents radicals of the formulae or

—L—O—CO—Q, in which
L represents a straight-chain or branched alkanediyl group with up to 6 carbon atoms,
Q represents $(C_1-C_6)$alkyl which is optionally substituted by carboxyl, or
represents radicals of the formulae

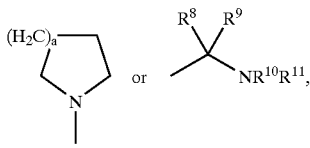

in which
a denotes the number 1 or 2,
$R^8$ denotes hydrogen,
$R^9$ denotes $(C_3-C_8)$cycloalkyl, $(C_6-C_{10})$aryl or hydrogen, or denotes $(C_1-C_8)$alkyl,
where the $(C_1-C_8)$alkyl is optionally substituted by cyano, methylthio, hydroxyl, mercapto, guanidyl or by a group of the formula $-NR^{12}R^{13}$ or $R^{14}-OC-$,
in which
$R^{12}$ and $R^{13}$ denote, independently of one another, hydrogen, $(C_1-C_8)$alkyl or phenyl, and
$R^{14}$ denotes hydroxyl, benzyloxyl, $(C_1-C_6)$ alkoxy or the abovementioned group $-NR^{12}R^{13}$,
or the $(C_1-C_8)$alkyl is optionally substituted by $(C_3-C_8)$-cycloalkyl or by $(C_6-C_{10})$aryl which is in turn substituted by hydroxyl, halogen, nitro, $(C_1-C_8)$alkoxy or by the group $-NR^{12}R^{13}$,
in which $R^{12}$ and $R^{13}$ have the meaning indicated above,
or the $(C_1-C_8)$alkyl is optionally substituted by a 5- to 6-membered nitrogen-containing heterocycle or by indolyl, in which the corresponding $-NH$ functions are optionally substituted by $(C_1-C_6)$alkyl or are protected by an amino protective group,
$R^{10}$ and $R^{11}$ are identical or different and denote hydrogen or an amino protective group,
$R^7$ represents hydrogen or represents a radical of the formula

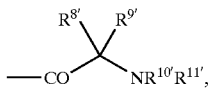

in which
$R^{8'}$, $R^{9'}$, $R^{10'}$ and $R^{11'}$ have the meaning indicated above for $R^8$, $R^9$, $R^{10}$ and $R^{11}$ and are identical to or different from the latter,
and the salts thereof.
2. Compounds according to claim 1 of the formulae

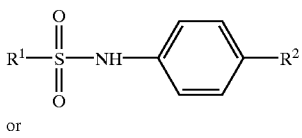

or

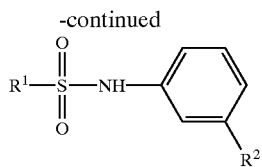

in which $R^1$ and $R^2$ have the meaning indicated above in claim 1.

3. Compounds of the general formula (I) according to claim 1, in which
$R^1$ represents a group selected from the formulae:

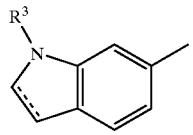

or

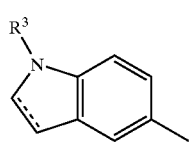

in which
---- represents a single or a double bond, and
$R^3$ has the meaning indicated above in claim 1,
and the salts thereof.

4. Compounds of the general formula (I) according to claim 1, in which
$R^3$ represents hydrogen, $(C_1-C_6)$alkyl or $(C_1-C_6)$ alkanoyl, and
$R^2$ represents

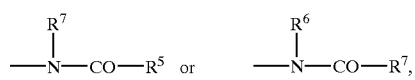

in which
$R^6$ is $(C_1-C_8)$alkyl which is optionally substituted by halogen or hydroxyl, and
$R^7$ is hydrogen,
and the salts thereof.

5. Compounds of the general formula (I) according to claim 1, in which $R^6$ is tert-butyl which is optionally substituted by halogen or hydroxyl, and the salts thereof.

6. Process for preparing the compounds of the formula (I) according to claim 1, characterized in that
(A) compounds of the general formula (II)

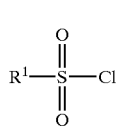

(II)

in which $R^1$ is as defined above in claim 1, are reacted with compounds of the general formula (III)

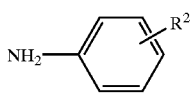 (III)

in which R² is as defined above in claim 1, to give compounds of the general formula (I), (B) compounds of the general formula (Ia)

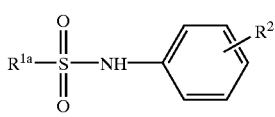 (Ia)

in which R² is as defined in claim 1, and
$R^{1a}$ represents a group selected from the following formulae:

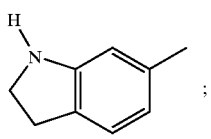

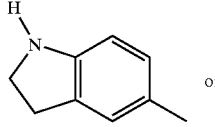

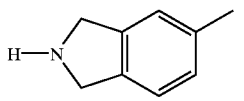

are reacted with compounds of the formula (IV)

 (IV)

in which R³ is as defined above in claim 1, and A is conventional leaving group in the presence of a base to give compounds of the general formula (Ib):

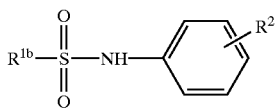 (Ib)

in which R² is as defined above in claim 1, and $R^{1b}$ represents a group selected from the following formulae:

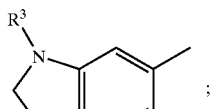

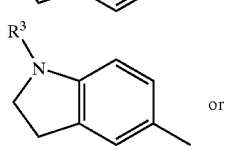

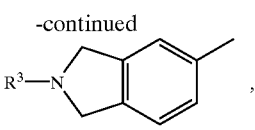

in which $R^{3a}$ is as defined above in claim 1, or (C) compounds of the general formula (Ic)

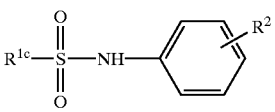 (Ic)

in which R² is as defined above in claim 1, and $R^{1c}$ represents a group selected from the following formulae:

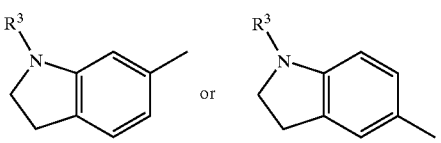

in which R³ is as defined above in claim 1, are converted by oxidation with DDQ (2,3-dichloro-5,6-dicyano-para-benzoquinone) into compounds of the general formula (Id):

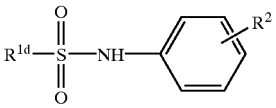 (Id)

in which R² is as defined above in claim 1, $R^{1d}$ represents a group selected from the following formulae:

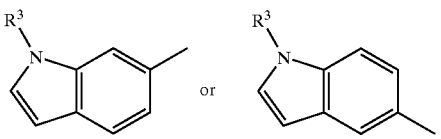

in which R³ is as defined above in claim 1, or (D) compounds of the general formula (Ie)

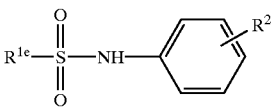 (Ie)

in which R² is as defined above in claim 1, and $R^{1e}$ has the following formulae:

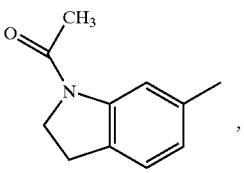

-continued

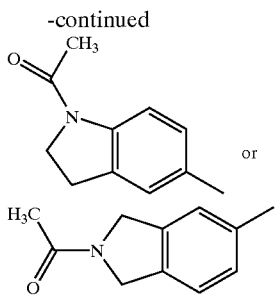

or

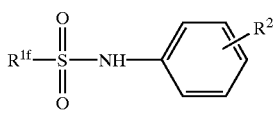

are reacted in the presence of water with alkali metal hydroxides to give compounds of the formula (Ia) which is as defined above in claim 1, or (E) compounds of the general formula (If)

(If)

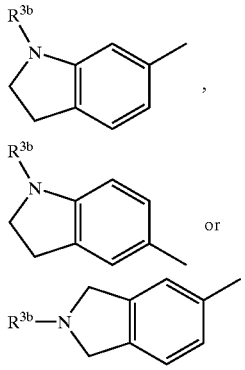

in which R is as defined above in claim 1, and $R^{1f}$ has the following formulae:

, or in which $R^{3b}$ represents $(C_1-C_6)$alkanoyl, are reacted with complex metal hydrides to give compounds of the general formula (Ig):

(Ig)

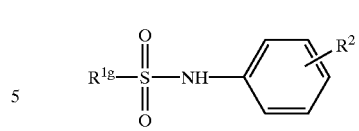

in which $R^2$ is as defined above in claim 1, and $R^{1g}$ has the following formulae:

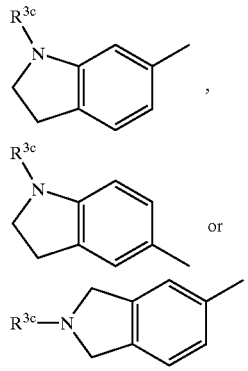

, or in which $R^{3c}$ represents $(C_1-C_6)$alkyl.

7. Pharmaceutical composition which comprises a compound of the general formula (I) according to claim 1 mixed with at least one pharmaceutically acceptable carrier or excipient.

8. A method of treating a viral infection, comprising administering to a mammal an effective amount of a compound of the general formula (I) according to claim 1.

9. The method of claim 8, wherein said viral infection is cytomegalovirus infection.

* * * * *